United States Patent [19]

Warriner

[11] Plant 4,089

[45] Aug. 2, 1977

[54] ROSE PLANT

[75] Inventor: William A. Warriner, Tustin, Calif.

[73] Assignee: Jackson & Perkins Co., Medford, Oreg.

[21] Appl. No.: 718,983

[22] Filed: Aug. 30, 1976

[51] Int. Cl.[2] ..... A01H 5/00

[52] U.S. Cl. ..... Plt./27

[58] Field of Search ..... Plt./27

*Primary Examiner*—Robert E. Bagwill

*Attorney, Agent, or Firm*—Klarquist, Sparkman, Campbell, Leigh, Hall & Whinston

[57] ABSTRACT

A novel floribunda rose variety having vigorous stems, steady bloom production, Phlox Pink blooms, and powdery mildew resistance.

1 Drawing Figure

1

This present invention relates to a new and distinct variety of rose plant of the floribunda class which was originated by me by crossing the variety Iceberg (unpatented) with pollen from an unnamed variety.

The primary objective of this breeding was to produce a new floribunda with characteristics similar to both parents, but phenotypically near a midpoint between the two parents. Iceberg is very bushy, well branched, white floribunda, the other parent, an unnamed variety, is an upright, heavily branched, red hybrid tea. The objective was substantially achieved in my new variety as evidenced by the following unique combination of characteristics which are outstanding in my new variety and which distinguish it from its parents as well as from all other varieties of which I am aware.

1. A very vigorous plant.
2. An upright structure of the canes with abundant branching, producing an almost unbroken continuity of bloom from spring to late autumn.
3. Blooms of low petalage, even form, the color of Phlox Pink (W).
4. Relatively good resistance to Rose Powdery Mildew.
5. Very little fragrance.
6. Abundant foliage giving a dense appearance to the plant.

Asexual reproduction of my new variety by budding, as performed at Wasco, Calif., proves that the foregoing characteristics reproduce true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed parent.*—Iceberg (Kordes).

*Pollen parent.*—Unnamed cultivar.

Classification:

*Botanical.*—Rosa hybrid.

*Commercial.*—Floribunda.

2

FLOWER

Observations made from specimens grown at Irvine, Calif., in October of 1975.

Blooming habit: Continuous.

Bud:

*Size.*—$\frac{3}{4}''$ to 1" when petals start to unfurl.

*Form.*—Long, pointed.

*Color.*—When sepals first divide near Phlox Pink (625/1); when half blown, upper side of petals mostly near Phlox Pink (625/1) with irregular areas near Phlox Pink (625/3), lower side of petals essentially the same color as upper side of petals.

*Sepals.*—Color: Outer surface near Scheeles Green (860) with some overlay of Garnet Brown (00918/3) with many stipitate glands; inner surface Scheeles Green (860/3) with much white tomentum. Three appendaged sepals lightly appendaged; two unappendaged sepals hairy edged.

*Receptacle.*—Color: Scheeles Green (860). Shape: parallel sided, deep funnel. Size: long. Surface: smooth, or slightly hairy.

*Peduncle.*—Length: short. Surface: glandular. Color: bronzy. Strength: stiff, erect.

*Opening.*—Petals recurve slightly.

Bloom:

*Size.*—Large. Average open size 3".

*Borne.*—Several together.

*Stems.*—Long, strong.

*Form.*—When first open, flat. Permanence, retains its form.

*Petalage.*—Number of petals under normal conditions, 14 to 20.

*Color.*—Center of flower: upper side of petals from Phlox Pink (625/3) at base of petals to Phlox Pink (625/2); reverse side of petals, near Phlox Pink (625/1); base of petals near white; general tonality from a distance Phlox Pink (625/2).

*Variegations.*—Some small areas of darker Phlox Pink (625) irregularly placed on petals.

*Discoloration.*—General tonality at end of first day, none; third day slight fading to Phlox Pink (625/2).

*Fragrance.*—Slight.

Petals:

*Texture.*—Thick.

*Shape.*—Nearly round.

*Form.*—Flat.

*Arrangement.*—Imbricated. Petaloids in center, few to none.

*Persistence.*—Drop off cleanly.

*Lastingness.*—On the plant, long. As cut flower, long.

Reproductive parts:

*Stamens, anthers.*—Large. Color, yellow. Arrangement, regular around styles.

*Filaments.*—Color: yellow.

*Pollen.*—Lemon yellow.

*Styles.*—Color: white.

*Stigmas.*—Color: yellow.

PLANT

Form: Bush.

Growth: Very vigorous, upright, branching.

Foliage: Number of leaflets on normal mid-stem leaves, 5 to 7.

*Size.*—Large.

*Quantity.*—Abundant.

*Color.*—New foliage: mostly Spinach Green (0960) with edges of Garnet Brown (00918/3); old foliage: Spinach Green (0960).

*Shape.*—Oval pointed.

*Texture.*—Upper side, leathery.

*Edge.*—Serrated.

*Serration.*—Single; small.

*Petiole.*—Rachis — Color: Reddish. Underside,

*Stipules.*—Long, mostly adnate; edges glandular.

*Disease resistance.*—Very resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Narrow base, hooked slightly downward.

*Color when young.*—Red.

*Position.*—Irregular. Numerous prickles on rachis in addition to many on stipitate glands.

Small prickles: None.

I claim:

1. A new and distinct variety of rose plant of the floribunda class, substantially as herein shown and described, characterized particularly as to novelty by the unique combination of its very vigorous growth, extremely free branching habit, continuity of blooms of a Phlox Pink (W) color, resistance to powdery mildew and little fragrance.

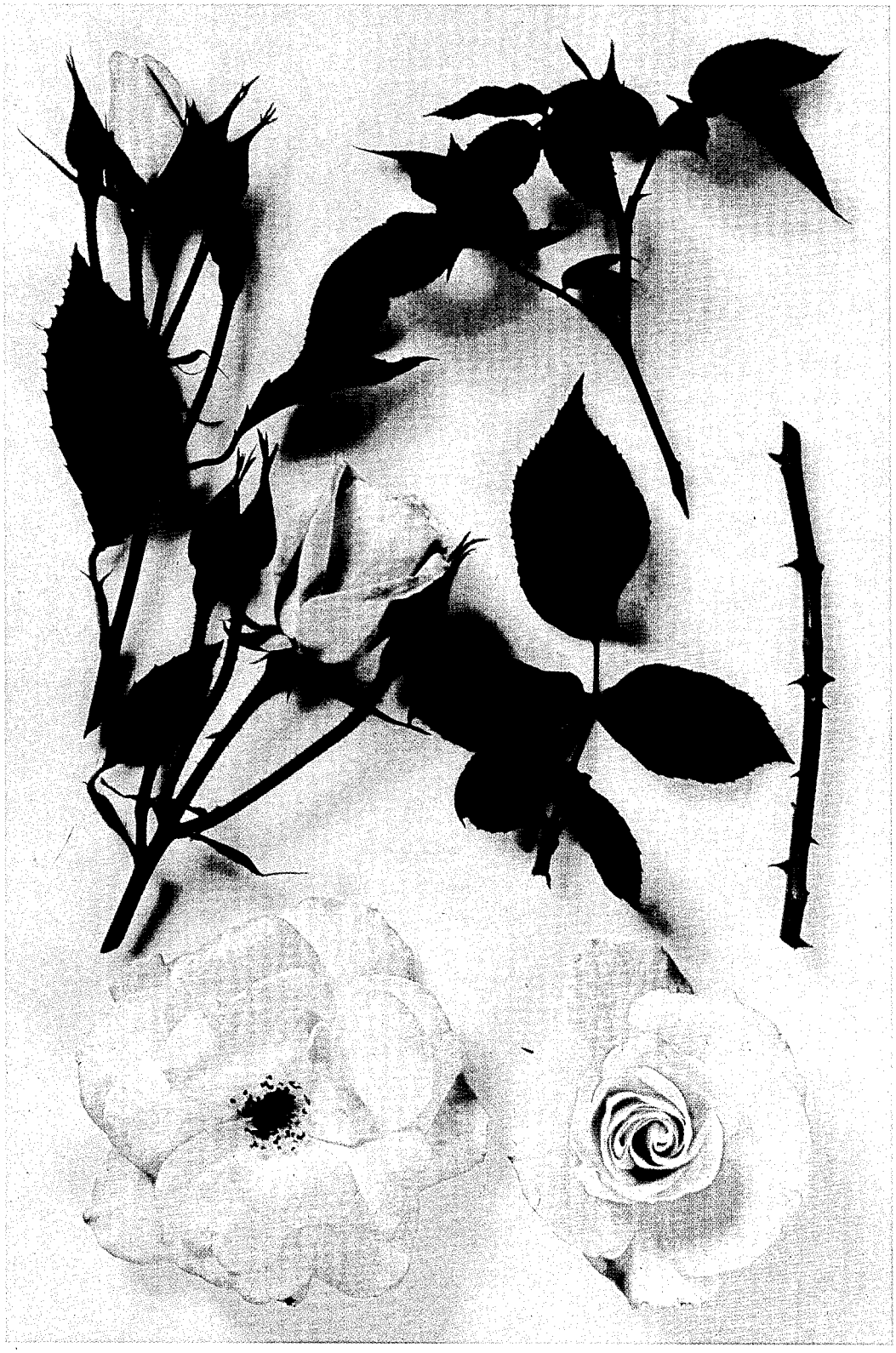

* * * * *